(12) United States Patent
Syfrig

(10) Patent No.: US 7,435,087 B2
(45) Date of Patent: Oct. 14, 2008

(54) ROOT EXTRACTION METHOD AND DEVICE

(76) Inventor: Benno Syfrig, Kauffmannweg 12, Luzern (CH) 6003

( * ) Notice: Subject to any disclaimer, the term of this patent is extended or adjusted under 35 U.S.C. 154(b) by 261 days.

(21) Appl. No.: 10/541,233

(22) PCT Filed: Dec. 27, 2003

(86) PCT No.: PCT/EP03/14923

§ 371 (c)(1),
(2), (4) Date: Jul. 1, 2005

(87) PCT Pub. No.: WO2004/060191

PCT Pub. Date: Jul. 22, 2004

(65) Prior Publication Data

US 2006/0166167 A1    Jul. 27, 2006

(30) Foreign Application Priority Data

Jan. 3, 2003  (CH) ............................ 2003 0004/03

(51) Int. Cl.
A61C 3/00  (2006.01)
(52) U.S. Cl. ..................................... 433/152
(58) Field of Classification Search ................ 433/152, 433/150, 151, 157, 158, 161, 153
See application file for complete search history.

(56) References Cited

U.S. PATENT DOCUMENTS

| 738,929 | A | * | 9/1903 | McMillin | 433/161 |
| 784,098 | A | * | 3/1905 | Beazley | 433/152 |
| 4,443,196 | A | | 4/1984 | Rico | |
| 5,209,747 | A | * | 5/1993 | Knoepfler | 606/16 |

FOREIGN PATENT DOCUMENTS

| DE | 101 36 762 | 10/2002 |
| FR | 735 071 | 11/1932 |
| WO | 02/078561 | 10/2002 |

* cited by examiner

Primary Examiner—Melba Bumgarner
(74) Attorney, Agent, or Firm—Wenderoth, Lind & Ponack, L.L.P.

(57) ABSTRACT

The invention relates to a method for extracting a root, whereby the root is extracted following a possible initial loosening of the root within the periodontal gap. A pin is inserted into the root and affixed there, whereafter a pulling element functionally linked with a tensioning device is connected with the pin. The pulling force required for extracting the root is subsequently applied to the root substantially in the direction of the axis of the tooth by means of the tensioning device that has been partially inserted into the mouth and supported there.

5 Claims, 2 Drawing Sheets

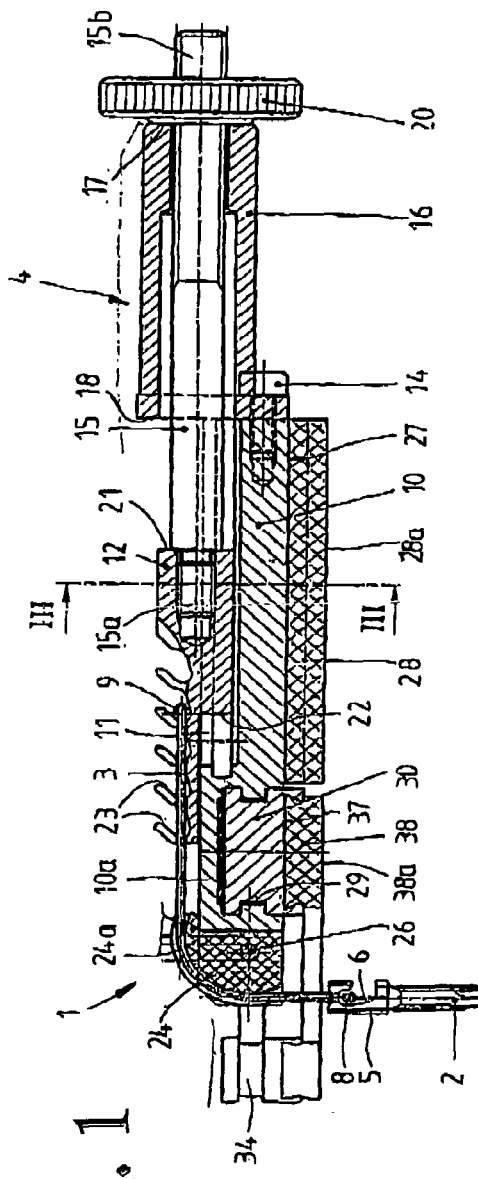

ROOT EXTRACTION METHOD AND DEVICE

BACKGROUND OF THE INVENTION

The invention relates to a method for extracting a root, as well as a device for applying the method.

In dental technology it is common that during the extracting of a tooth and following the administering of a local anaesthetic, the root is first loosened somewhat inside the gum with a tool that is pushed into the periodontal gap, and the tooth is then pulled out with pliers together with the root. This does however become problematic if the tooth is broken or if the same is covered with a crown, where practically no grip surface is available for the pliers, and if only the root alone is to be extracted.

It is the purpose of this invention to provide a method for the simple extraction of a root and a device for applying the method.

SUMMARY OF THE INVENTION

This task is solved in accordance with the invention by a method and a device for applying the method.

Further preferred embodiments of the method of this invention as well as the device of this invention form the subject of the following description.

A pin is inserted into the root and affixed there for extracting the same. Then, a pulling element functionally linked with a manually activatable tensioning device is inserted into the pin. Subsequently, the pulling force required for extracting the tooth is created and applied to the root substantially in the axial direction of the same by means of the supported tensioning device partially inserted into the mouth. Thus, a relative large pulling force can be applied to the root without need of excessive force and without space problems and a risk of possible injury within the mouth. The device of this invention is simple and cost-effective, and enables easy handling.

BRIEF DESCRIPTION OF THE DRAWINGS

The invention will now be explained with reference to the drawings, whereby:

FIG. 1 shows a longitudinal cross-section of an embodiment of a device of this invention for extracting a root;

FIG. 2 shows an overview of the device illustrated in FIG. 1;

DETAILED DESCRIPTION OF THE INVENTION

FIG. 1 shows a device 1 for extracting a root, incorporating a pin 2 that can be inserted into the root and affixed there, a pulling element 3 that can be inserted into the pin 2, and a tensioning device 4 functionally linked with the pulling element 3.

The pin 2 of the embodiment illustrated here takes the form of a threaded pin which is screwed into the tooth, root, preferably in the direction of its axis. However, other means for affixing the pin 2 to the tooth root could, be envisaged (this could, for example, consist of a cement or adhesive connection or an expanding pin). In addition, the insertion in the direction of the axis of the root is sometimes not possible, or no longer possible, for example when the root is not straight or is already equipped with one or two screws for the fitting of a crown.

Figure 4:
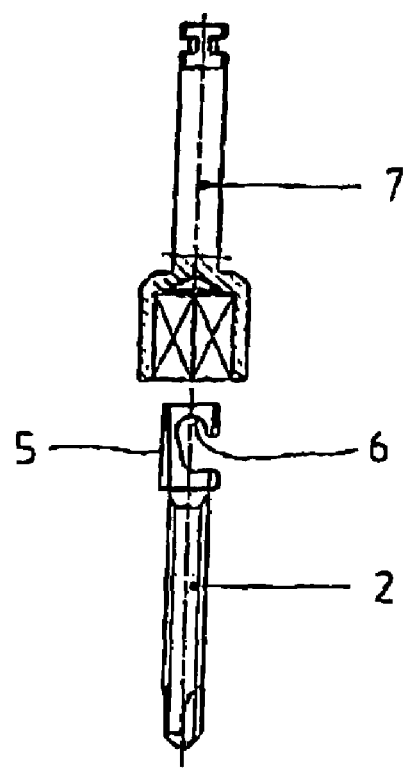
FIG. 4 shows a threaded pin as part of the device of this invention, with a counter piece for screwing the threaded pin into the root.

The pin 2 is equipped with a bead 5, which is in turn equipped with a hook-shaped recess 6. As indicated in FIG. 4, the head 5 is preferably equipped with an external shape (square) of the type that makes it possible to screw a standardized adapter 7 into the root, onto which the head 5 can be affixed.

The pulling element 3 already mentioned above is then hooked into the hook-shaped recess 6 with a cross pin 8. The pulling element 3 can, for example, take the form of a flexible element such as a wire, a string, or a rope. At the other end of the pulling element 3, a cross pin 9 is also provided, with which the pulling element 3 can be affixed to the tensioning device 4 as is described in more detail below.

The tensioning device 4 incorporates a stretched base body 10 which, in turn, has a guide groove 11 with a T-shaped cross section for a tensioning support 12 that is longitudinally adjustable in relation to the base body 10. A threaded bolt 15 extending in a longitudinal direction has a front end 15a screwed into the tensioning support 3.2, whereby a rear threaded part 15b is guided through a support sleeve 16 screwed onto the rear end of the base body 10 by means of screws 14. A ribbed nut 20 is provided on the threaded part 15b, the same being supportable at a rear facing surface 17 of the support sleeve 16. The tensioning support 12 can be supported in its longitudinal direction with a rear surface 21 against a front facing surface 18 of the support sleeve 16 on the one hand, and with a surface 22 located towards the front against a front base body part 10a on the other hand.

The tensioning support 12 is equipped with a number of hook-shaped recesses 23 arranged on behind the other in longitudinal direction, onto which the pulling element 3 can be hooked with the cross pin 9. A diverting part 24 for the pulling element 3 is affixed to the front base body part 10a. The pulling element 3 is held to extend substantially in an axial direction of the root in relation to the pin 3 on the one hand, and is also tensioned at a right angle to the axial direction of the root in a longitudinal direction of the tensioning device 4 on the other hand, and rests on the diverting part 24. The diverting part 24 takes the form of a firmly affixed disc segment, the cross section of which forms a guide nut 24a for the pulling element 3, and the pulling element 3 is affixed in a front side, fork-shaped part 25 of the front base body part 10a by means of a cross pin 26.

Figure 3:
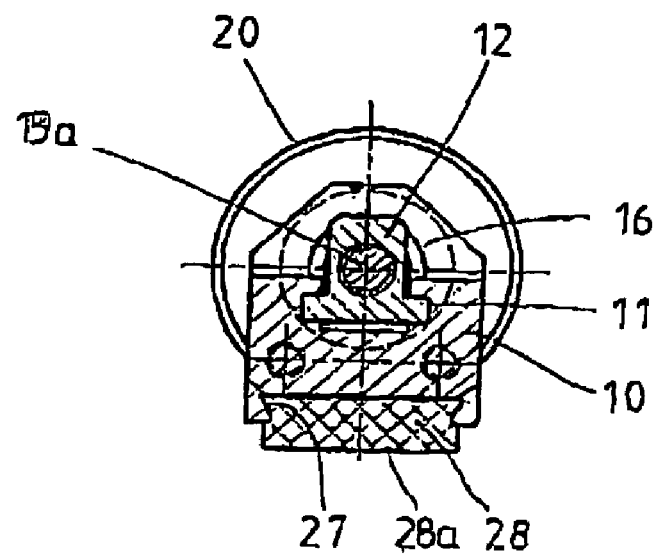
FIG. 3 shows a cross-sectional view along the line III-III in FIG. 1.

On the side that faces away from the guide groove 11 for the tensioning support 12, the base body 10 is equipped with a groove 27 with a dovetail cross-section (sec especially FIG. 3), into which a support plate 28 made of plastic is inserted. The front base body section 10a also incorporates a groove 29 for receiving a rotating segment 30 as illustrated in FIG. 1 on the same side of the base body 10, and the axis of the segment 30 extends diagonally with respect to the displacement direction of the tensioning support 12, and the segment 30 can be inserted from the side into the groove 29. The groove 29 forms the guide surfaces for an external as well as an internal circumference surface 32 of the rotating segment 30. For this, the groove 29 is placed in the front base body section 10a in such a way that the pulling element extending to the pin 2 extends coaxially in relation to the rotating segment 30. The rotating segment 30 forms a cut-out defined by surfaces 34, 35, whose alignment can be changed, i.e. adjusted by turning the rotating segment 30. The rotating segment 30 is—much like the base body 1.0 with the support plate 28—equipped with a support disc 38 made of plastic, which is inserted into a groove 37 of the rotating segment 30 with a dovetail cross-section (FIG. 1). The support plate 28 and the support disc 38 each have a resting surface 28a, 38a for supporting the tensioning device 4 in the mouth.

When a root is to be extracted, the pin 2 is first inserted into the root and affixed there, preferably screwed into the same. One end of the pulling element 3 is then inserted into (attached to) the pin 2, for example by being hooked into the recess 6 with the cross pin 8, and affixed to the tensioning device 4 that has been inserted into the mouth and is partially supported there with the other end. With the selection of a suitable recess 23 for hooking therein the other cross pin 9, the position of the location in the mouth that is to be treated (i.e., the distance between the supporting point of the tensioning device in the mouth and the root to be extracted) must be considered and a suitable pre-tensioning of the pulling element 3 created. The position of the tensioning support 12 between the front base body part 10a and the front facing surface 18 of the support sleeve 16 sets the starting position prior to creating the actual pulling force for extracting the root, and can also be quickly adjusted by means of axially adjusting the ribbed nut 20 to suit the threaded part 15b. With the rear surface 21 of the tensioning support 12 abutting against the front facing surface 18 of the support sleeve 16, the axial distance of the ribbed nut 20 from the rear facing surface 17 of the support sleeve 16 determines the path along which the tensioning support 12 can be quickly moved in a longitudinal direction without rotating the ribbed nut 20. The actual pulling force for extracting the root is then created by the ribbed nut 20 abutting against the rear facing surface 17 of the support sleeve 16 by turning the nut 20, and the subsequently created slow adjustment of the threaded part, i.e. tensioning support. For this, it is of advantage that a relatively large pulling force can be created via the thread without excessive force. In addition, the diverting (directional change) of the pulling element 3 and the right-angled arrangement of the tensioning support 12 in relation to the pin 2 affixed onto the root means that the root is pulled substantially in the direction of the axis of the root without creating space problems or a possible risk of injury within the mouth.

The support of the tensioning device 4 is carried out by means of the support surface 28a of the support plate 28 (on the edge of the mouth) and via the support surface 38a of the support disc 38 affixed to the rotating segment 30 (for the location to be treated). The turnable rotating segment 30 can be adjusted to suit the relevant local conditions around the location that is to be treated in order to guarantee optimized support.

The fast adjustment of the tensioning support 12 already mentioned, which is limited in its maximum size by the abutment of the tensioning support 12 against the support sleeve 16 on one side, and by the front base body section 10a on the other side, whereby the size can be adjusted (i.e. reduced by means of the ribbed nut 20) can also be used for pre-treating. In other words, the root can be loosened by a reciprocal movement of the tensioning support to apply a sudden impact force on the root prior to applying the actual pulling force. It is of course also possible when required to carry out a loosening in the periodontal gap by means of a suitable tool in the known way.

The device of this invention is simple and cost-effective, and enables easy handling. The base body 10 of the tensioning device 4 can for example be held with the thumb and middle finger of one hand, whereby the index finger supports the positioning of the pulling element 3 on the diverting part 24, and the ribbed nut 20 is activated with the other hand. In principle, the pulling force could also be applied mechanically.

It is possible to envisage means which effect a sudden impact upon the pulling element 3 during the turning of the ribbed nut 20. For example, the facing surface 17 of the support sleeve 16 and the ribbed nut abutting against the same 20 can be equipped with corresponding radially extending saw teeth or suchlike. During the turning of the ribbed nut, an additional increase can therefore be created across a certain angle, which is then decreased again.

The invention claimed is:

1. A method of extracting a root of a tooth, comprising:
   inserting a pin into the root and affixing the pin to the root;
   connecting a flexible pulling element to the pin affixed to the root by hooking the pulling element into the pin, the pulling element comprising one of a wire, a string, or a rope bent at a substantially right angle along a diverting part, the pulling element being functionally linked to a tensioning device; hooking the pulling element into the tensioning device; pre-tensioning the pulling element between the pin and the tensioning device before hooking the pulling element to the pin or the tensioning device;
   applying a pulling force to the root via the pulling element using the tensioning device so as to extract the root, wherein the pulling force is transmitted from a portion of the pulling element at the diverting part to the root via the pulling element in a direction substantially parallel to the longitudinal axis of the root, and is transmitted from the tensioning device to the portion of the pulling element at the diverting part via the pulling element in a direction substantially perpendicular to the longitudinal axis of the root, the tensioning device being partially inserted into and supported in the mouth;
   wherein said pre-tensioning of the pulling element comprises adjusting a tensioning support moveable substantially at a right angle in relation to the longitudinal axis of the root, the tensioning support being adjustable in relation to a base body of the tensioning device; and
   loosening the root by sudden activation of the tensioning support prior to said applying the pulling force to extract the root.

2. The method of claim 1, wherein said applying the pulling force to extract the root comprises turning a ribbed nut engaging a threaded bolt connected to the tensioning support, the threaded bolt being supported on a base body.

3. The method of claim 1, wherein said affixing the pin to the root comprises inserting a threaded pin into the root along the longitudinal axis of the root.

4. The method of claim 1, wherein said connecting the flexible pulling element to the pin comprises connecting a first end of the pulling element to the pin, a second end of the pulling element opposite the first end being functionally linked to the tensioning device, the diverting part being located between the first end and the second end.

5. The method of claim 1, further comprising initial loosening of the root within the periodontal gap before said applying the pulling force to extract the root.

* * * * *